United States Patent
Duncan et al.

(10) Patent No.: US 7,622,621 B2
(45) Date of Patent: Nov. 24, 2009

(54) PREPARATION OF ALKYLAROMATIC HYDROCARBONS AND ALKYLARYL SULFONATES

(75) Inventors: Carolyn B. Duncan, Franklin, GA (US); David Wayne Turner, Raymond, ME (US); Jane C. Cheng, Bridgewater, NJ (US); Charles M. Yarbrough, Baton Rouge, LA (US); Raphael Frans Caers, Edegem (BE); Ramzi Y. Saleh, Baton Rouge, LA (US); James L. Propp, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 675 days.

(21) Appl. No.: 10/509,508

(22) PCT Filed: Mar. 28, 2003

(86) PCT No.: PCT/US03/09517

§ 371 (c)(1),
(2), (4) Date: Sep. 28, 2004

(87) PCT Pub. No.: WO03/082782

PCT Pub. Date: Oct. 9, 2003

(65) Prior Publication Data

US 2005/0165264 A1    Jul. 28, 2005

Related U.S. Application Data

(60) Provisional application No. 60/369,232, filed on Mar. 29, 2002, provisional application No. 60/368,928, filed on Mar. 29, 2002, provisional application No. 60/368,917, filed on Mar. 29, 2002.

(51) Int. Cl.
C07C 2/66 (2006.01)
C07C 2/12 (2006.01)

(52) U.S. Cl. .................. 585/323; 585/467; 585/533

(58) Field of Classification Search .......... 585/467, 585/323, 533
See application file for complete search history.

(56) References Cited

U.S. PATENT DOCUMENTS

| | | | |
|---|---|---|---|
| 4,076,842 A | 2/1978 | Plank et al. | 423/328 |
| 4,298,547 A | 11/1981 | Young | 260/505 |
| 4,439,409 A | 3/1984 | Puppe et al. | 423/328 |
| 4,826,667 A | 5/1989 | Zones et al. | 423/277 |
| 4,954,325 A | 9/1990 | Rubin et al. | 423/328 |
| 4,962,256 A * | 10/1990 | Le et al. | 585/467 |
| 5,026,933 A | 6/1991 | Blain et al. | 585/7 |
| 5,236,575 A | 8/1993 | Bennett et al. | 208/46 |
| 5,250,277 A | 10/1993 | Kresge et al. | 423/329.1 |
| 5,258,566 A | 11/1993 | Kresge et al. | |
| 5,362,697 A | 11/1994 | Fung et al. | 502/71 |
| 5,401,896 A | 3/1995 | Kuehl et al. | |
| 5,849,960 A | 12/1998 | Singleton et al. | |
| 6,077,498 A | 6/2000 | Diaz Cabanas et al. | 423/702 |
| 6,274,540 B1 | 8/2001 | Scheibel et al. | 510/352 |
| 6,306,817 B1 | 10/2001 | Kott et al. | 510/535 |

FOREIGN PATENT DOCUMENTS

| | | |
|---|---|---|
| EP | 0293032 | 7/1993 |
| WO | WO 97/17290 | 5/1997 |

OTHER PUBLICATIONS

Myers, Drew, Surfactant Science and Technology, pp. 82-85, VCH Publishers, Inc. (New York, N.Y. USA) 1988, USBN 0-89573-399-0.

* cited by examiner

Primary Examiner—Thuan Dinh Dang
(74) Attorney, Agent, or Firm—Darryl M. Tyus

(57) ABSTRACT

In a process for preparing an alkylaromatic hydrocarbon composition an olefinic hydrocarbon mixture and an aromatic compound are contacted under alkylation conditions with an aromatic alkylation catalyst selected from a homogeneous acid catalyst and heterogeneous acid catalyst comprising a molecular sieve having an X-ray diffraction pattern including d-spacing maxima at 12.4±0.25, 6.9±0.15, 3.57±0.07 and 3.42±0.07 Angstroms. The olefinic hydrocarbon mixture comprises at least 5 wt % by weight of mono-olefin oligomers of the empirical formula:

$$C_nH_{2n}$$

wherein n is greater than or equal to 10, the mono-olefin oligomers comprising at least 20 percent by weight of olefins having at least 12 carbon atoms, and the olefins having at least 12 carbon atoms having an average of from 0.8 to 2.0 $C_1$-$C_3$ alkyl branches per carbon chain. Sulfonation of the alkylaromatic hydrocarbon product produces an alkylaryl sulfonate mixture that exhibits advantageous properties, such as biodegradability and hard and cold water performance.

9 Claims, No Drawings

PREPARATION OF ALKYLAROMATIC HYDROCARBONS AND ALKYLARYL SULFONATES

CROSS REFERENCE TO RELATED APPLICATIONS

This application is a National Stage Application of International Application No. PCT/US03/095 17, filed Mar. 28, 2003, which claims the benefit of Provisional Application No. 60/369,232, filed Mar. 29, 2002, Provisional Application No. 60/368,928, filed Mar. 29, 2002, and Provisional Application No. 60/368,917 filed Mar. 29, 2002. These applications are incorporated herein by reference.

FIELD

This invention relates to the preparation of alkylaromatic hydrocarbon compositions and the use of such compositions in the production of alkylaryl sulfonates.

BACKGROUND

Historically, highly branched alkylbenzenesulfonate surfactants, such as those based on tetrapropylene (known as "ABS") were used in detergents. However, these highly branched materials were found to exhibit very poor biodegradability. As a result, subsequent efforts at improving manufacturing processes for alkylbenzenesulfonates were mainly directed at making the alkyl moieties as linear as practically possible. Thus the overwhelming proportion of a large volume of prior art relating to alkylbenzenesulfonate surfactant manufacture is directed to the objective of achieving linearity. Moreover all large-scale commercial alkylbenzenesulfonate processes in use today are directed to the production of linear alkylbenzenesulfonates ("LAS"). Typically, these processes involve initially alkylating benzene with a linear olefin in the presence of a homogeneous acid catalyst, such as $AlCl_3$ or HF, and then sulfonating the alkylated benzene.

However, current linear alkylbenzenesulfonates have significant limitations in that, for example, they have limited hard water and/or cold water cleaning properties. Thus, LAS surfactants often fail to produce good cleaning results, for example when formulated with non-phosphate builders and/or when used in hard water areas.

As a result of the limitations of LAS surfactants, consumer cleaning formulations frequently include higher levels of cosurfactants, builders, and other additives than would be needed with a superior alkylbenzenesulfonate. Accordingly, it would be desirable to simplify detergent formulations and deliver both better performance and better value to the consumer. Moreover, in view of the very large volumes of alkylbenzenesulfonate surfactants and detergent formulations used worldwide, even modest improvements in performance of the basic alkylbenzenesulfonate detergent would be of great significance in the marketplace.

In contrast with the conventional understanding as to the importance of linearity in alkylbenzenesulfonates, U.S. Pat. No. 5,026,933 teaches that lightly branched olefin oligomers produced by the oligomerization of lower olefins over surface-deactivated ZSM-23 can be used to alkylate benzene to produce long chain alkylbenzenes which, when sulfonated, yield surfactants which exhibit similar biodegradability properties to equivalent LAS materials. The '933 patent teaches that the alkylation catalyst required to achieve these advantageous results is a heterogeneous crystalline zeolite catalyst having a pore size of 6 to 7 Angstrom, such as dealuminated mordenite.

More recent work reported in, for example, U.S. Pat. No. 6,274,540, has confirmed the findings in the '933 patent and demonstrated that alkylaryl sulfonate surfactants having good biodegradability and cold water solubility can be produced from alkylaromatic hydrocarbon mixtures in which the alkyl moieties have a main chain with 5 to 20 carbons atoms and one or more crystallinity-disrupting groups. The alkylaryl sulfonate surfactants have a Krafft Temperature of no more than 40° C., preferably no more than 5° C., a percentage biodegradation exceeding that of tetrapropylene benzene sulfonate, a weight ratio of nonquaternary to quaternary carbon atoms in the alkyl moiety of at least 5, preferably at least 100, and contain at least 60 wt %, and preferably at least 80 wt %, of isomers in which the aryl group is attached to the second or third carbon atom of the primary alkyl chain.

Similar results are reported in U.S. Pat. No. 6,306,817 in which the alkylaryl sulfonate is composed of at least 2 isomers each having an acyclic aliphatic chain with 6 to 20 carbon atoms and at least one $C_1$-$C_3$ side chain, a weight ratio of nonquaternary to quaternary carbon atoms in the alkyl moiety of at least 10, preferably at least 100, a weight loss of no more than 40 wt %, preferably no more than 10 wt %, in a Hardness Tolerance test, and containing at least 60% of isomers in which the aryl group is attached to the second and third carbon atoms of the primary alkyl chain. According to the '817 patent, the preferred alkylaryl sulfonate consists entirely of isomers in which the aryl group is attached to the second and third carbon atoms of the primary alkyl chain, but no directions are provided as to how to achieve this result.

Typically the surfactants disclosed in the '540 and '817 patents are produced by alkylating an aromatic compound, such as benzene or toluene, with a skeletally isomerized linear olefin in the presence of a mordenite catalyst.

In accordance with the present invention, it has now been found that by using different catalysts from those disclosed in the '933, '540 and '817 patents, it is possible to alkylate an aromatic compound with lightly branched olefin oligomers to produce alkylaromatic compositions which, when sulfonated, produce alkylarylsulfonate surfactants having improved properties, such as biodegradability and hard and cold water performance, as compared with conventional LAS products.

SUMMARY

Accordingly, the invention resides in a first aspect in a process for preparing an alkylaromatic hydrocarbon composition comprising contacting a feedstock comprising an olefinic hydrocarbon mixture and an aromatic compound under alkylation conditions with an aromatic alkylation catalyst selected from a homogeneous acid catalyst and heterogeneous acid catalyst comprising a molecular sieve having an X-ray diffraction pattern including d-spacing maxima at 12.4±0.25, 6.9±0.15, 3.57±0.07 and 3.42±0.07 Angstroms, said olefinic hydrocarbon mixture comprising at least 5% by weight of mono-olefin oligomers of the empirical formula:

$$C_nH_{2n}$$

wherein n is greater than or equal to 10, wherein said mono-olefin oligomers comprise at least 20% by weight of olefins having at least 12 carbon atoms and said olefins having at least 12 carbon atoms have an average of from 0.8 to 2.0 $C_1$-$C_3$ alkyl branches per carbon chain.

Conveniently, said olefinic hydrocarbon mixture comprises of at least 20%, such as at least 80%, by weight of said mono-olefin oligomers.

Conveniently, said mono-olefin oligomers are produced by oligomerizing an olefin selected from propene, butene and mixtures thereof over surface-deactivated ZSM-23.

In one embodiment, said homogeneous acid catalyst is a Lewis acid catalyst or a Brønsted acid catalyst.

In another embodiment, the molecular sieve is selected from MCM-22, PSH-3, SSZ-25, ERB-1, ITQ-1, ITQ-2, MCM-36, MCM-49 and MCM-56.

Typically, the aromatic compound is benzene or toluene.

In one embodiment, said mono-olefin oligomers comprise from about 50% to about 98% by weight of olefins having less than or equal to 12 carbon atoms and from about 2% to about 50% by weight of olefins having more than 12 carbon atoms.

In a second aspect, the invention resides in an alkylaromatic hydrocarbon composition produced by the process of said first aspect of the invention.

In a third aspect, the invention resides in an alkylaromatic hydrocarbon mixture comprising a plurality of alkylaromatic hydrocarbons each having:

(a) at least 12 carbon atoms in its alkyl side chain,
(b) an average of from 0.8 to 2.0 $C_1$-$C_3$ alkyl branches per alkyl side chain and no branches in said alkyl side chain other than $C_1$-$C_3$ alkyl,
(c) an average of less than 0.1 quaternary carbon atoms in said alkyl side chain and
(d) at least 95% of the aromatic species being located at the 2- or 3-position in the alkyl side chain.

In a fourth aspect, the invention resides in an alkylaryl sulfonate mixture produced by sulfonating the alkylaromatic hydrocarbon composition produced the process of said first aspect of the invention.

In a fifth aspect, the invention resides in an alkylarylsulfonate mixture comprising a plurality of alkylarylsulfonate compounds each having:

(a) at least 12 carbon atoms in its alkyl side chain,
(b) an average of from 0.8 to 2.0 $C_1$-$C_3$ alkyl branches per alkyl side chain and no branches in said alkyl side chain other than $C_1$-$C_3$ alkyl,
(c) an average of less than 0.1 quaternary carbon atoms in said alkyl side chain,
(d) at least 95% of the aromatic species being located at the 2- or 3-position in the alkyl side chain,
(e) a Krafft temperature below 10° C. and
(f) a hard water insolubility of less than 1 wt %.

In a sixth aspect, the invention resides in a process for preparing an alkylaryl sulfonate mixture comprising the steps of:

(a) contacting a first feedstock comprising a first olefinic hydrocarbon mixture and an aromatic compound under alkylation conditions with an aromatic alkylation catalyst to produce a first alkylaromatic hydrocarbon composition, said first olefinic hydrocarbon mixture comprising at least 5% by weight of mono-olefin oligomers having the empirical formula:

$$C_nH_{2n}$$

wherein n is greater than or equal to 10 and less than or equal to 12 and having an average of from 0.8 to 2.0 $C_1$-$C_3$ alkyl branches per carbon chain;

(b) contacting a second feedstock comprising a second olefinic hydrocarbon mixture and an aromatic compound under alkylation conditions with an aromatic alkylation catalyst to produce a second alkylaromatic hydrocarbon composition, said second olefinic hydrocarbon mixture comprising at least 5% by weight of mono-olefin oligomers having the empirical formula:

$$C_nH_{2n}$$

wherein n is greater than 12 and having an average of from 0.8 to 2.0 $C_1$-$C_3$ alkyl branches per carbon chain;

(c) forming a mixture comprising about 50% to about 98% by weight of said first alkylaromatic hydrocarbon composition and about 2% to about 50% by weight of said second alkylaromatic hydrocarbon composition; and
(d) sulfonating the mixture produced in step (c).

DETAILED DESCRIPTION OF THE EMBODIMENTS

The present invention provides a process for alkylating an aromatic compound with an olefinic hydrocarbon mixture comprising lightly branched olefin oligomers in the presence of an homogeneous acid catalyst or an MCM-22 family molecular sieve to produce a long chain alkyl aromatic hydrocarbon mixture which, when sulfonated, produces an alkylarylsulfonate surfactant which exhibits advantageous biodegradability and hard and cold water solubility properties.

Feedstocks

The term "aromatic" is used herein in accordance with its art-recognized scope which includes alkyl substituted and unsubstituted mono- and polynuclear compounds. Substituted aromatic compounds, which can be alkylated herein, must possess at least one hydrogen atom directly bonded to the aromatic nucleus. Suitable aromatic hydrocarbons include benzene, toluene, xylene and naphthalene, with preferred compounds being benzene and toluene.

The olefinic hydrocarbon mixture used in the alkylation process of the invention comprises at least 5%, such as at least 20%, for example at least 80% by weight of mono-olefin oligomers of the empirical formula:

$$C_nH_{2n}$$

wherein n is greater than or equal to 10 and wherein said mono-olefin oligomers comprise at least 20 wt %, and such as at least 60 wt %, of olefins having at least 12 carbon atoms and said olefins having at least 12 carbon atoms have an average of from 0.8 to 2.0, such as 0.8 to 1.3, $C_1$-$C_3$ alkyl branches per carbon chain. Typically, the olefins having at least 12 carbon atoms contain no branches other than $C_1$-$C_3$ normal alkyl groups and normally no branches other than methyl or ethyl groups.

An olefinic hydrocarbon mixture comprising at least 95 wt % of said mono-olefin oligomers can be produced by oligomerizing propylene and/or n-butene over a catalyst comprising ZSM-23 which has been surface deactivated, preferably by treatment with a sterically hindered nitrogenous base, such as a trialkyl pyridine compound, for example 2,4,6-collidine (2,4,6-trimethyl pyridine, gamma-collidine). The surface deactivating compound should have a minimum cross-section diameter greater than the effective pore size of the zeolite to be treated; i.e., greater than 5 Angstroms. ZSM-23 and its characteristic X-ray diffraction pattern are described in detail in U.S. Pat. No. 4,076,842, the entire contents of which are incorporated herein by reference. In one practical embodiment, the ZSM-23 employed in the catalyst has an alpha value of about 25 and a crystal size of less than 0.1 micron and is conveniently composited with a binder, such as alumina.

Suitable oligomerization conditions include a temperature of about 160 to about 250° C., a pressure of about 500 to about 1500 psig (3550 to 10450 kPa) and a WHSV of 0.1 to about 4.0. Conveniently, where surface deactivation is achieved by treatment with a trialkyl pyridine compound, the feed to the oligomerization process includes additional trialkyl pyridine compound so that the surface properties of the zeolite are maintained during the process. In addition, the oligomerization feed can contain paraffins which can, for example, be added in amounts in excess of 80% by weight of the total olefin and paraffin content to act as a heat sink during the oligomerization process. Further details of the oligomerization process and product can be found in U.S. Pat. No. 5,026,933, the entire contents of which are incorporated herein by reference.

By fractionating the olefinic hydrocarbon mixture produced by the oligomerization process, it is possible to produce a plurality of olefinic fractions of different molecular weight. For example, by fractionating the product obtained by oligomerizing a butene-containing feed, a $C_{12}$ olefinic fraction and a $C_{16}$ olefinic fraction can be separated. These fractions can then be mixed in the desired proportions to obtain a desired alkylation feed for use in the alkylation process of the invention.

For example, it has been found that one advantageous alkylation feed is a mixture of mono-olefin oligomers comprising from about 50% to about 98%, such as from about 50% to about 70%, by weight of olefins having less than or equal to 12 carbon atoms and from about 2% to about 50%, from about 30% to about 50%, by weight of olefins having more than 12 carbon atoms. In one practical embodiment, the mixture of mono-olefin oligomers comprises from about 55% to about 65% by weight of olefins having about 12 carbon atoms and from about 35% to about 45% by weight of olefins having about 16 carbon atoms.

In addition to the lightly branched mono-olefin oligomers described above, the olefinic hydrocarbon mixture employed in the alkylation process of this invention can contain up to 95 wt % of other $C_{10}$+ olefins, such as linear alpha-olefins.

Alkylation Process

The alkylation process of this invention is conducted such that the organic feedstock, i.e., the aromatic compound and the olefinic hydrocarbon mixture, are contacted under effective alkylation conditions with an aromatic alkylation catalyst.

In one embodiment, the catalyst is a homogeneous acid catalyst such as a Lewis acid catalyst, for example aluminum chloride. Alternatively, the homogeneous acid catalyst is a Brønsted acid catalyst, such as HF or phosphoric acid.

Suitable alkylation conditions with a homogeneous catalyst include a temperature of from about −10° C. to about 100° C., a pressure of from about 1.0 to about 25 atmospheres, a feed weight hourly space velocity (WHSV) of from about 0.2 $hr^{-1}$ to about 10 $hr^{-1}$ and an aromatic compound to olefinic hydrocarbon mixture mole ratio of from about 1:1 to about 15:1. Typical reaction conditions include a temperature of from about 0° C. to about 50° C., a pressure of from about 1.0 to about 3.0 atmospheres, a feed weight hourly space velocity (WHSV) of from about 0.1 $hr^{-1}$ to about 0.5 $hr^{-1}$ and an aromatic compound to olefinic hydrocarbon mixture mole ratio of from about 5:1 to about 10:1.

In a further embodiment, the alkylation process is conducted in the presence of a heterogeneous acid catalyst comprising a molecular sieve having an X-ray diffraction pattern including d-spacing maxima at 12.4±0.25, 6.9±0.15, 3.57±0.07 and 3.42±0.07 Angstrom. The X-ray diffraction data used to characterize said molecular sieve are obtained by standard techniques using the K-alpha doublet of copper as the incident radiation and a diffractometer equipped with a scintillation counter and associated computer as the collection system. Materials having the required X-ray diffraction lines are sometimes referred to a molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 is described in European Patent No. 0293032, ITQ-1 is described in U.S. Pat. No. 6,077,498, ITQ-2 is described in International Patent Publication No. WO97/17290, MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference. The molecular sieve can be combined in conventional manner with an oxide binder, such as alumina, such that the final alkylation catalyst contains between 2 and 80 wt % sieve.

It is to be appreciated the MCM-22 family molecular sieves described above are distinguished from conventional large pore zeolite alkylation catalysts, such as mordenite, in that catalysis in MCM-22 materials occurs in 12-ring surface pockets which do not communicate with the 10-ring internal pore system of the molecular sieve.

In addition, it has been found that MCM-22 family molecular sieve catalysts are highly selective to the production of alkylaromatic products in which the aromatic compound is bonded to the long chain alkyl group at the second and/or the third position in the chain. In fact, using the oligomerized olefinic hydrocarbon mixture described above, it is found that the alkylation process can produce alkylaromatic products in which at least 95%, and normally in excess of 98%, of the aromatic compounds are bonded to the second and/or the third carbons in the alkyl chain. In addition, it is found that any highly branched or cyclic olefins which may be present in the hydrocarbon mixture are generally too large to access the catalytic sites of the molecular sieve catalyst employed in the alkylation process of the invention and hence do not react with the aromatic feed to produce unwanted impurities. For this reason, it is generally unnecessary to subject the product of the oligomerization step to any pretreatment, other than washing to remove the organic nitrogen surface deactivating agent, prior to feeding the product to the alkylation step.

With a molecular sieve catalyst, suitable alkylation conditions include a temperature of from about 0° C. to about 500° C., a pressure of from about 0.2 to about 250 atmospheres, a feed weight hourly space velocity (WHSV) of from about 0.1 $hr^{-1}$ to about 500 $hr^{-1}$ and an aromatic compound to olefinic hydrocarbon mixture mole ratio of from about 1:1 to about 20:1. The WHSV is based upon the weight of the catalyst composition employed, i.e., the total weight of active catalyst (and binder if present). Typical reaction conditions include a temperature within the range of from about 100° C. to about 350° C., a pressure of from about 1 to about 25 atmospheres, a WHSV of from about 0.5 $hr^{-1}$ to about 100 $hr^{-1}$ and an aromatic compound to olefinic hydrocarbon mixture mole ratio of from about 4:1 to about 15:1.

The alkylation process of the invention can be conducted with reactants in either the vapor phase or the liquid phase. In addition, the reactants can be free from intentional admixture or dilution with other materials, or they can be brought into contact with the catalyst composition with the aid of carrier gases or diluents such as, for example, hydrogen or nitrogen. In particular, the organic feedstock can also contain up to 80 wt % paraffins, which may, for example, have been added to act as a heat sink in the oligomerization process.

The alkylation process described herein can be carried out as a batch-type, semi-continuous or continuous operation.

Alkylaromatic Products

The alkylation process of the invention produces alkylaromatic hydrocarbon products which are particularly useful as intermediates in the production of alkylaryl sulfonate detergents or surfactants.

Moreover, where the alkylation catalyst comprises an MCM-22 family molecular sieve, the alkylation process of the invention produces a novel alkylaromatic hydrocarbon mixture comprising a plurality of alkylaromatic hydrocarbons each having:

(a) at least 12 carbon atoms in its alkyl side chain,
(b) an average of from 0.8 to 2.0 $C_1$-$C_3$ alkyl branches per alkyl side chain and no branches in said alkyl side chain other than $C_1$-$C_3$ alkyl,
(c) an average of less than 0.1 quaternary carbon atoms in said alkyl side chain and
(d) at least 95% of the aromatic species being located at the 2- or 3-position in the alkyl side chain.

Alkylaryl Sulfonate Products

Processes for sulfonating alkylbenzenes are described in the U.S. Pat. No. 4,298,547, the entire contents of which are incorporated herein by reference. More particularly, the alkylaromatic hydrocarbon composition produced by the alkylation process of the invention may be converted to an alkylaryl sulfonate mixture by sulfonation of the aromatic ring with sulfuric acid. The sulfonation reaction is well known in the art and is commonly carried out by contacting the organic compound with sulfuric acid at temperatures of from about −70° C. to about +60° C. Detailed descriptions of specific commercial processes abound in the literature. See, for instance, pages 60-62 of INDUSTRIAL CHEMICALS, Third Edition, by W. L. Faith et al, published by John Wiley & Sons, Inc.

The product resulting from the sulfonation process is an alkylaryl sulfonate mixture which exhibits improved properties, such as biodegradability and hard and cold water performance, as compared with conventional LAS products.

In particular, where the sulfonation process is conducted on the novel alkylaromatic mixture obtained using an MCM-22 family alkylation catalyst, the product is a novel alkylaryl sulfonate mixture comprising a plurality of alkylaryl sulfonate compounds each having:

(a) at least 12 carbon atoms in its alkyl side chain,
(b) an average of from 0.8 to 2.0 $C_1$-$C_3$ alkyl branches per alkyl side chain and no branches in said alkyl side chain other than $C_1$-$C_3$ alkyl,
(c) an average of less than 0.1 quaternary carbon atoms in said alkyl side chain,
(d) at least 95% of the aromatic species being located at the 2- or 3-position in the alkyl side chain,
(f) a Krafft temperature below 10° C. and
(g) a hard water insolubility of less than 1 wt %.

"Krafft temperature" refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, Surfactant Science and Technology, pp. 82-85, VCH Publishers, Inc. (New York, N.Y., USA), 1988 (ISBN 0-89573-399-0), which is incorporated by reference herein in its entirety.

The hard water insolubility of the alkylaryl sulfonate compounds are obtained by a test in which different concentrations of $Ca(Cl)_2$ solutions and surfactant solutions are combined, frozen, and heated to 25° C. and 40° C. for 48 hours. Each equilibrated sample is observed for precipitation at the end of 48 hours and a precipitation phase boundary of [$Ca^{++}$] vs. [Surfactant] is generated for 25° C. and 40° C. at surfactant concentrations above and below the critical micelle concentration (CMC). The result is reported as wt. % Ca++ required to form a precipitate at high surfactant concentration (0.2 Molar Surfactant).

Where alkylaryl sulfonate mixture is produced by sulfonating an alkylaromatic hydrocarbon composition obtained by alkylation of an aromatic hydrocarbon a mixture of lightly branched olefinic fractions of different molecular weight, it is found that the product has excellent biodegradability together with an unique combination of a low critical micelle concentration and good hard and cold water solubility properties. In particular, the alkylaryl sulfonate mixture exhibits a Krafft temperature below 10° C. and a hard water insolubility of less than 1 wt %.

It is, however, to be appreciated that such an advantageous alkylaryl sulfonate mixture can also be produced by separately alkylating the aromatic compound with the different olefinic fractions, mixing the resulting alkylaromatic fractions in the weight ratios described above and then sulfonating the resultant alkylaromatic mixture. In other words, the aromatic compound can be alkylated with an olefinic fraction having less than or equal to 12 carbon atoms to produce a first alkylaromatic composition and separately alkylated with an olefinic fraction having more than 12 carbon atoms to produce a second alkylaromatic composition. A mixture comprising about 50% to about 98%, preferably about 50% to about 70%, and more preferably about 55% to about 65%, by weight of first alkylaromatic composition and from about 2% to about 50%, preferably about 30% to about 50%, and most preferably about 35% to about 45%, by weight of the second alkylaromatic composition is then produced and sulfonated to generate the desired alkylaryl sulfonate mixture.

The invention will now be more particularly described with reference to the following Examples.

EXAMPLE 1

A ZSM-23 catalyst which had been treated with 2,4,6-collidine in the manner described in U.S. Pat. No. 5,026,933 was used to oligomerize a butene feed containing 2-50 ppm of collidine at a temperature of 235° C. at the hotspot, a pressure of 1000 psig (7000 kPa) and a WHSV of 1.2. The product of the oligomerization process fractionated into separate $C_8$, $C_{12}$ and $C_{16}$ olefin fractions and was found to contain about 45 wt % $C_8$ olefins, about 35 wt % $C_{12}$ olefins and about 10 wt % $C_{16}$ olefins. The average degree of branching of the $C_8$, $C_{12}$ and $C_{16}$ olefin fractions was determined by NMR and found to be 1, 1.1 and 1.2 respectively. No branching other than methyl and ethyl branching was detected.

EXAMPLE 2

The $C_{12}$ and $C_{16}$ olefin fractions produced by the process of Example 1 and a commercially available linear $C_{12}$ n-olefin were used to alkylate benzene using an MCM-22 catalyst. The conditions used in the tests and the results obtained after 24 hours on-stream are summarized in Table 1 below:

TABLE 1

|  | n-$C_{12}$ olefin | Example 1 $C_{12}$ fraction | Example 1 $C_{16}$ fraction |
|---|---|---|---|
| Grams of Olefin | 56.0 | 56.0 | 56.0 |
| Grams of Benzene | 390 | 390 | 293 |
| Benzene: Olefin Molar Ratio | 15 | 15 | 15 |

TABLE 1-continued

|  | n-$C_{12}$ olefin | Example 1 $C_{12}$ fraction | Example 1 $C_{16}$ fraction |
|---|---|---|---|
| Pressure (psig) | 150 | 150 | 150 |
| Temperature (° C.) | 180 | 180 | 180 |
| Conversion (%) | 96.3 | 91.0 | 87.2 |
| Monoalkylation Selectivity (%) | 97.4 | 92.1 | 90.7 |
| Unreacted Olefin (%) | 3.7 | 9.0 | 12.8 |
| Monoalkylbenzene (%) | 93.8 | 83.8 | 79.0 |
| Heavies (%) | 2.5 | 7.2 | 8.1 |
| 2- + 3-Phenyl Isomers (%) | 80.33 | 98.0 | 95.27 |
| Quaternary C/alkyl chain | 0 | 0 | 0 |

The phenyl isomer distributions given in Table 1 were obtained by G.C. mass spectrometry using chemical ionization to allow the major fragments to be identified and measured. The quaternary carbon concentrations were determined by NMR.

From the above results it will be seen that, although the olefin oligomers of Example 1 were slightly less reactive than the linear $C_{12}$ olefin, monoalkylation activity remained high with oligomers of Example 1 and more importantly the selectivity to isomers in which the phenyl group was located at the 2- and 3-positions on the alkyl chain was much higher with the oligomers of Example 1 as compared with the linear $C_{12}$ olefin.

EXAMPLE 3

The $C_{12}$ alkylphenyl products from Example 2 were sulfonated in a falling film plug flow reactor in which an air/$SO_3$ stream is contacted with the organic phase under the following conditions:

| | |
|---|---|
| Alkylbenzene flow rate = | 3.6 g/min; |
| $SO_3$ flow rate = | 1.2 g/min; |
| Reactor gas inlet temperature = | about 38° C.; |
| Reactor alkylbenzene inlet temperature = | about 26° C. |

As air/$SO_3$ and alkylbenzene move down the reactor, the $SO_3$ is absorbed and is complexed or reacted. Exiting the reactor, the mixture enters a cyclone where the gas and liquid phases are separated. The liquid alkylbenzene sulfonic acid is then neutralized to form the alkylbenzene sulfonate, sodium salt. The performance of the resultant products as surfactants is summarized in Table 2.

TABLE 2

|  | n-$C_{12}$ olefin alkylate | Alkylate from Ex. 1 $C_{12}$ fraction |
|---|---|---|
| Average Molecular Weight | 332 | 332 |
| Critical Micelle Conc. (38° C.) | 465 ± 66 ppm | 764 ± 300 ppm |
| Krafft Temperature (° C.) | 17.5 | 9.4 |
| Hard Water Insolubility (%) | 0.16 | 0.07 |
| Biodegradability (estimated) | 65% | 65% |

EXAMPLE 4

922 g of benzene and 13.4 g of anhydrous $AlCl_3$ were placed in a 3-liter round bottom flask equipped with overhead condenser, addition funnel, and a mechanical stirrer. The flask was placed in an ice-bath set at 6-8° C. The addition funnel was charged with 176 g of the $C_{12}$ olefin fraction from Example 1. After the flask temperature reached 6-8° C., the olefin was added drop wise over a period of about 90 minutes. The total benzene to $C_{12}$ olefin molar ratio in this experiment was 11.27. Throughout the experiment, the flask was well stirred and the temperature was maintained at 6-8° C. Immediately after all the olefin was added to the flask, a small sample of the reaction mixture was withdrawn, and further samples were withdrawn every hour thereafter. The samples were quenched with water and the organic layer was analyzed by GC to measure olefin conversion, and selectivity to monoalkylates, dialkylates and other by-products. The results are summarized in Table 3.

TABLE 3

| Time after initial sample, hours | Initial sample | 1.00 |
|---|---|---|
| Conversion (wt %) | 96.20 | 95.97 |
| Total Alkylbenzenes (wt %) | 82.18 | 85.89 |
| Dialkylbenzenes (wt %) | 16.02 | 12.69 |
| Heavies (wt %) | 1.79 | 1.43 |

EXAMPLE 5

Example 4 was repeated and the results are summarized in Table 4.

TABLE 4

| Time after initial sample, hours | Initial sample | 1.00 |
|---|---|---|
| Conversion (wt %) | 96.04 | 95.82 |
| Total Alkylbenzenes (wt %) | 84.85 | 85.93 |
| Dialkylbenzenes (wt %) | 13.71 | 12.32 |
| Heavies (wt %) | 1.45 | 1.75 |

EXAMPLE 6

In the above Examples 4 and 5, the total benzene to olefin ratio was 11.27 molar. In this example, the same experiment was repeated except samples from the flask were withdrawn as the olefin was added in order to examine the effect of varying the benzene/olefin ratio on alkylate selectivity and isomer distribution. Samples were withdrawn after 1/4, 2/4, 3/4, and 4/4 of the olefin was added corresponding to benzene/$C_{12}$ olefin ratios of 45.05, 22.54, 15.03, and 11.27, respectively. The results are summarized in Table 5.

TABLE 5

| Bz/C12 ratio | 45.05 | 22.54 | 15.03 | 11.27* | 11.27** |
|---|---|---|---|---|---|
| Conversion (wt %) | 97.02 | 96.46 | 95.98 | 95.94 | 95.45 |
| Total Alkylbenzene (wt %) | 93.11 | 90.58 | 89.39 | 83.65 | 86.92 |
| Dialkylbenzenes (wt %) | 6.54 | 8.27 | 9.21 | 14.36 | 11.45 |
| Heavies (wt %) | 0.35 | 1.15 | 1.40 | 1.99 | 1.63 |

*Immediately after all C12 added
**1 hr after all C12 added.

The alkylate isomer distributions of samples from Example 5 were determined by G.C. mass spectrometry using chemical ionization to allow the major fragments to be identified and measured. The results are plotted in FIG. 1 as a function of benzene to olefin molar ratio. It will be seen from FIG. 1 that at least 50 wt % of the alkylates were composed of 2-phenyl and 3-phenyldodecanes which are known to produce sulfonates having good biodegradability and excellent performance in detergent applications.

EXAMPLE 7

A $C_{12}$ alkylphenyl product similar to that obtained in Examples 4 to 6 was sulfonated using the procedure of Example 3. The performance of the resultant product as a surfactant is compared with that of a conventional $C_{12}$ LAS in Table 6.

TABLE 6

|  | $C_{12}$ LAS | Invention |
| --- | --- | --- |
| Critical Micelle Conc. (38° C.) | 950 ppm | 1162 ± 300 ppm |
| Krafft Temperature (° C.) | <0 | 3.5 |
| Water Hardness Tolerance (wt %) | 0.003 | 0.03 |
| Biodegradability (estimated) |  | 60% |

It will be seen that the alkylaryl sulfonate produced by the process of Example 7 exhibited similar detergent, biodegradability and cold water performance to the conventional LAS product but had ten times the water hardness tolerance of the conventional product.

EXAMPLE 8

The products of the alkylation process of Example 2 were distilled, and the $C_{12}$ alkylbenzene and $C_{16}$ alkylbenzene fractions were collected. A portion of the resultant $C_{16}$ alkylbenzene fraction was then blended with a portion of the $C_{12}$ alkylbenzene fraction at a 60:40 weight percent ratio of $C_{12}$ alkylbenzene to $C_{16}$ alkylbenzene. The resultant $C_{12}/C_{16}$ alkylphenyl product was sulfonated as in Example 3 and the performance of the resultant product as a surfactant is compared with those obtained with the individual molecular weight fractions in Table 7.

TABLE 7

|  | Example 2 | Example 3 | Example 4 |
| --- | --- | --- | --- |
| Average Molecular Weight | 332 | 332 | 354.4 |
| Critical Micelle Conc. (38° C.) | 1162 ± 300 ppm | 764 ± 300 ppm | 106 ± 35 ppm |
| Krafft Temperature (° C.) | 3.5 | 9.4 | 9.4 |
| Hard Water Insolubility (%) | 0.03 | 0.07 | 0.05 |
| Biodegradability (Estimated) | 60% | 65% | 62% |

It will be seen from the results in Table 7 that the product of Example 8, a blend of $C_{12}$ and $C_{16}$ alkylbenzene sulfonates, had a much lower critical micelle concentration than either of the products obtained using the $C_{12}$ olefin fraction or $C_{16}$ olefin fraction alone but retained the good hard and cold water properties of the products of Example 3. It is expected that the results obtained by first blending the $C_{12}$ and $C_{16}$ olefin fractions to make the alkylbenzenes would be the same as those obtained by blending the $C_{12}$ and $C_{16}$ alkylbenzenes fractions.

The invention claimed is:

1. A process for preparing an alkylaromatic hydrocarbon composition comprising the steps of:

(a) oligomerizing an olefin selected from propylene, n-butene and mixtures thereof, over a catalyst comprising ZSM-23 and a surface deactivating agent, to form an oligomerization product comprising at least 95% by weight of mono-olefin oligomers of the empirical formula:

$$C_nH_{2n}$$

wherein n is greater than or equal to 10, wherein said mono-olefin oligomers comprise at least 20% by weight of olefins having at least 12 carbon atoms and said olefins having at least 12 carbon atoms have an average of from 0.8 to 2.0 $C_1$-$C_3$ alkyl branches per carbon chain;

(b) contacting the oligomerization product and an aromatic compound under alkylation conditions with an aromatic alkylation catalyst comprising a molecular sieve having an X-ray diffraction pattern including d-spacing maxima at 12.4+0.25, 6.9+0.15, 3.57+0.07, and 3.42+0.07 Angstroms, said molecular sieve is selected from the group consisting of MCM-22, PSH-3, SSZ-25, ERB-1, ITQ-1, ITQ-2, MCM-36, MCM-49, and MCM-56, wherein the oligomerization product is not subject to any pretreatment other than to remove the surface deactivating agent prior to the contacting step.

2. The process of claim 1 wherein said olefins having at least 12 carbon atoms have an average of from 0.8 to 1.3 $C_1$-$C_3$ alkyl branches per carbon chain.

3. The process of claim 1 wherein said olefinic hydrocarbon mixture comprises at least 20% by weight of said mono-olefin oligomers.

4. The process of claim 1 wherein said mono-olefin oligomers comprise from about 50% to about 98% by weight of olefins having less than or equal to 12 carbon atoms and from about 2% to about 50% by weight of olefins having more than 12 carbon atoms.

5. The process of claim 1 wherein said olefinic hydrocarbon mixture also contains linear alpha-olefins containing at least 10 carbon atoms.

6. The process of claim 1 wherein said feedstock also comprises up to 80 wt % of paraffins.

7. The process of claim 1 wherein said alkylation conditions include a temperature of from 100° C. to about 350° C., a pressure of about 1 to about 25 atmospheres, a WHSV of about 0.5 $hr^{-1}$ to about 100 $hr^{-1}$ and an aromatic compound to olefinic hydrocarbon mixture mole ratio of about 1:1 to about 20:1.

8. The process of claim 1 wherein said alkylation conditions include a temperature of from about −10° C. to about 50° C., a pressure of from about 1.0 to about 5.0 atmospheres, a feed weight hourly space velocity (WHSV) of from about 0.2 $hr^{-1}$ to about 10 $hr^{-1}$ and an aromatic compound to olefinic hydrocarbon mixture mole ratio of from about 1:1 to about 15:1.

9. The process of claim 1 wherein said aromatic compound is selected from the group consisting of benzene and toluene.

* * * * *

UNITED STATES PATENT AND TRADEMARK OFFICE
CERTIFICATE OF CORRECTION

| | | |
|---|---|---|
| PATENT NO. | : 7,622,621 B2 | Page 1 of 1 |
| APPLICATION NO. | : 10/509508 | |
| DATED | : November 24, 2009 | |
| INVENTOR(S) | : Duncan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1164 days.

Signed and Sealed this

Twenty-sixth Day of October, 2010

David J. Kappos
*Director of the United States Patent and Trademark Office*